United States Patent [19]

Chatterton et al.

[11] Patent Number: 5,175,332

[45] Date of Patent: Dec. 29, 1992

[54] CYCLOALKOXYSILANES

[75] Inventors: Wayne J. Chatterton, Midland; Sean P. Davern, Auburn; Carl A. Fairbank; Terrence K. Hilty, both of Midland, all of Mich.

[73] Assignee: Dow Corning Corporation, Midland, Mich.

[21] Appl. No.: 807,314

[22] Filed: Dec. 16, 1991

[51] Int. Cl.$^5$ .......................... C07F 7/08; C07F 7/18
[52] U.S. Cl. .................................. 556/482; 556/442; 556/483
[58] Field of Search .................... 556/482, 483, 492

[56] References Cited

U.S. PATENT DOCUMENTS

| | | | |
|---|---|---|---|
| 4,585,885 | 4/1986 | Bernhard et al. | 556/482 X |
| 4,958,041 | 9/1990 | Graefe et al. | 556/480 |
| 5,086,146 | 2/1992 | Liles et al. | 556/482 X |

Primary Examiner—Paul F. Shaver
Attorney, Agent, or Firm—Alexander Weitz

[57] ABSTRACT

A cycloalkoxysilane, having utility as an electron donor in the Ziegler-Natta polymerization of olefinic monomers, of the structure $$(R'O)_x(R')_y Si(OR)_{4-x-y}$$

wherein R is independently selected from the group consisting of alkyl radicals having 1 to 5 carbon atoms and acyl radicals having 2 to 5 carbon atoms, R' is independently selected from the group consisting of a cyclopentyl radical, a cyclohexyl radical a cycloheptyl radical, and substituted radicals thereof, x is 1, 2, 3 or 4 and y is 0, 1 or 2.

10 Claims, No Drawings

CYCLOALKOXYSILANES

FIELD OF THE INVENTION

The present invention relates to novel silanes, more particularly cycloalkoxysilanes wherein the cycloalkyl radical is selected from substituted or unsubstituted cyclopentyl cyclohexyl or cycloheptyl groups.

BACKGROUND OF THE INVENTION

The use of certain dialkyldialkoxysilanes as stereomodifiers in Ziegler-Natta type catalysts is known in the polymerization of various olefinic monomers. The preparation of specific silane compounds of this type is disclosed by U.S. Pat. No. 4,958,041 to Graefe et al., wherein said silanes are represented by the general formula

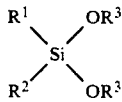

in which $R^1$ and $R^2$ each represent an alkyl or cycloalkyl group having 3 to 10 carbon atoms and $R^3$ is independently selected from alkyl radicals having 1 to 5 carbon atoms. Graefe et al. teach that these materials are selectively produced by reacting a tetralkoxysilane or a monoorganotrialkoxysilane with a Grignard reagent having the structure. e.g., $R^1MgCl$. This prior art citation specifically teaches away from the use of the typical solvents employed in Grignard reaction, such as tetrahydrofuran, in favor of dialkyl ethers, such as methyl-tert-butylether, in order to attain essentially quantitative yields of the products. The patent to Graefe et al. does not teach or suggest the formation of the cycloalkoxysilanes of the present invention and applicants have not been able to find reference to the particular compounds, described infra, in the open literature.

SUMMARY OF THE INVENTION

The present invention therefore relates to a cycloalkoxysilane having the structure $$(R'O)_x(R')_y Si(OR)_{4-x-y} \qquad (I)$$

wherein R is independently selected from the group consisting of alkyl radicals having 1 to 5 carbon atoms and acyl radicals having 2 to 5 carbon atoms, R' is independently selected from the group consisting of a cyclopentyl radical, a cyclohexyl radical a cycloheptyl radical, and substituted radicals thereof, x is 1, 2, 3 or 4 and y is 0, 1 or 2.

DETAILED DESCRIPTION OF THE INVENTION

The group R of the cycloalkoxysilane represented by formula (I) above is independently selected from the group consisting of alkyl radicals having 1 to 5 carbon atoms, such as methyl, ethyl, isopropyl, butyl and pentyl, and acyl radicals having 2 to 5 carbon atoms, such as acetyl, propionyl and butyryl. It is preferred that R is an alkyl radical having 1 to 5 carbon atoms, most preferably a methyl radical. The independently selected group R' in formula (I) is a monovalent substituted or unsubstituted cycloalkyl radical which contains five to seven carbon atoms in its ring. Thus, this group may be a cyclopentyl radical, a cyclohexyl radical or a cycloheptyl radical. cyclopentyl being preferred. Alternatively, R' can be one of the above mentioned radical wherein one or more ring hydrogen atoms is substituted with an alkyl radical having 1 to 5 carbon atoms, an alkoxy radical having 1 to 5 carbon atoms, an aryl group, an aryloxy group or a halogen atom, inter alia. Thus, for example, substituted cyclopentyl groups include such structures as

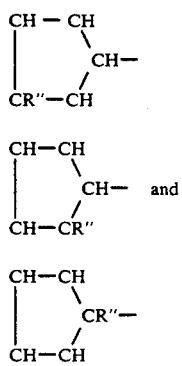

in which R" is one of the above stated alkyl, alkoxy, aryl, aryloxy or halogen groups. When the ring has substitution thereon, it is preferred that the substituent be selected from methoxy or ethoxy radicals.

For the purposes of the present invention, x in formula (I) is an integer having a value of 1 to 4. inclusive. Preferably, x is 1 or 2. Likewise, y is an integer having a value of 0 to 2. inclusive. Preferably, y is 0 or 1.

Highly preferred cycloalkoxysilanes of the invention have the structures

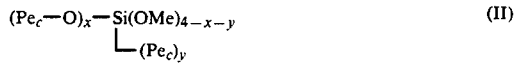

in which Me and $Pe_c$ hereinafter denote a methyl radical and a cyclopentyl radical, respectively, x is 1 or 2 and y is 0 or 1.

The cycloalkoxysilanes of the present invention may be prepared by at least two routes. The first of these is a trans-etherification reaction wherein a cycloalkyl alcohol is reacted with a silane according to the equation

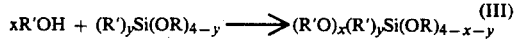

wherein R, R', x and y have their above defined meanings. This reaction can be accelerated by the application of heat or the addition of a catalytic quantity of magnesium metal or an acid, such as concentrated hydrochloric acid or nitric acid. This route does not require the use of a solvent or a special environment and is a preferred method for preparing cycloalkoxysilanes of the invention when y of formula (I) is zero. In equation (III), the alcohol R'OH is preferably added to the silane over a protracted period, such as two hours, at an elevated temperature, such as 100° to 150° C. Under these conditions, it has been observed that an essentially quantitative yield is obtained (i.e., in the range of 95%+ of the product based on starting materials).

The second route for the preparation of the cycloalkoxysilane compounds of the invention involves the initial formation of a Grignard reagent according to the reactions described by equations (IV) and (V).

$$2 Mg + CH_2Cl_2 \rightarrow ClMgCH_2MgCl \qquad (IV)$$

$$ClMgCH_2MgCl + 2 R'OH \rightarrow 2 R'OMgCl + CH_4 \qquad (V)$$

wherein R' has its previously defined meaning. The reaction represented by equation (IV) can be carried out in an organic solvent such as tetrahydrofuran, 1,4-dioxane or an ether such as diethyl ether, preferably at a temperature of 25° to 60° C., whereupon the alcohol R'OH is slowly added to the reaction mixture according to reaction (V) and the methane byproduct is stripped off. Again, these reactions are essentially quantitative and yields of the Grignard R'OMgCl in the range of 95%+ are obtained under such conditions. This Grignard reagent is then reacted with a silane according to equation (VI) to produce the cycloalkoxysilane:

$$R'OMgCl + (R')_y Si(OR)_{4-y} \rightarrow (R'O)_x(R')_y Si(OR)_{4-x-y} \qquad (VI)$$

wherein R, R', x and y have their previously defined meanings. Reactions (IV) through (VI) are preferably carried out in a dry inert atmosphere, such as nitrogen or argon, to prevent side reactions of the Grignard reagents with moisture. A reaction temperature of 0° to 150° C. may be used but is, of course, limited by the boiling point of the solvent in the system. Preferably, this reaction is carried out at approximately 60° C. As before, this reaction is also essentially quantitative and yields of 95% to 99% cycloalkoxysilane are typically achieved under the preferred conditions. The reaction scheme of equation (VI) is preferably employed when y in formula (I) is one.

The cycloalkoxysilane compounds of the present invention find utility as intermediates for the preparation of other silicone compounds and compositions and they are particularly useful as electron donors in the Ziegler-Natta catalyzed polymerization of olefinic monomers in the production of plastics such as polyethylene, polypropylene, polybutadiene and polybutylene.

EXAMPLES

The following examples are presented to further illustrate the preparation of the cycloalkoxysilanes of this invention, but are not to be construed as limiting the invention, which is delineated in the appended claims. All parts and percentages in the examples are on a weight basis and all measurements were obtained at 25° C. unless indicated to the contrary.

EXAMPLE 1

To a three liter flask equipped with a stirrer, thermometer and a condenser there was added one liter of tetrahydrofuran (THF) and 85 grams (3.5 moles) of magnesium turnings while the contents were blanketed under an argon atmosphere. An addition funnel was filled with 225 ml (3.5 moles) of dichloromethane and this component was introduced at a rate of 5 ml/minute at a pot temperature of 28° C. The contents of the flask were then heated to about 60° C. and a few iodine crystals were added to initiate the Grignard reaction. After all the magnesium was consumed, 86.13 grams (1 mole) of cyclopentyl alcohol was added and reacted at a temperature of about 60° C. for a period of about 3 hours, the byproduct methane produced in this phase of the reaction being removed by evaporating it through the condenser and purging with argon. The above solution was then stripped and the Grignard reagent was isolated. The structure of this compound was confirmed using a combination of infrared and gas chromatography/mass spectrometry techniques to be $Pe_cOMgCl$, wherein $Pe_c$ hereinafter denotes a cyclopentyl radical. The yield was estimated to be about 80% based on an acid titration of the Grignard.

EXAMPLE 2

One hundred and fifteen grams of the Grignard formed in Example 1 (0.80 mole) was slowly added to 121 grams (0.80 mole) of tetramethoxysilane at room temperature/2 hours under an argon blanket using 250 ml of THF solvent. The resultant compound was isolated and confirmed to have the structure $Pe_cOSi(OMe)_3$, wherein Me hereinafter denotes a methyl radical. The boiling point of the product was determined as 84° C. at 22 mm Hg and the calculated yield was about 70%.

EXAMPLE 3

Thirteen grams (0.1 mole) of a previously prepared Grignard having the formula $Pe_cMgCl$ was slowly added to 21 grams (0.1 mole) of the $Pe_cOSi(OMe)_3$ formed in Example 2 dissolved in 150 ml of THF. This reaction was carried out at 110° C./3 hours under an argon blanket. The product contained two main components: about 60% of a silane having the confirmed structure $$\begin{array}{c} Pe_cOSi(OMe)_2 \\ | \\ Pe_c \end{array}$$

about 40% of a silane having the structure $(Pe_c)_2Si(OMe)_2$.

EXAMPLE 4

Into a one liter three-necked flask there was placed 16.3 grams (0.1071 mole) of tetramethoxysilane, no particular effort being made to exclude ambient atmosphere. An addition funnel was filled with 20.2 grams (0.2345 mole) of cyclopentyl alcohol. The alcohol was rapidly added to the flask and the contents stirred while heating at 120° C. Some magnesium turnings were then added to accelerate the reaction. After 1.5 hours, the reaction mixture was filtered and distilled to afford a 95% yield of a compound having a boiling point of 64° C. at 2 mm Hg and having the confirmed structure $(Pe_cO)_2Si(OMe)_2$.

EXAMPLE 5

The procedures of Example 4 were repeated wherein the molar ratio of cyclopentyl alcohol to tetramethoxysilane was 1:1 to prepare a compound having a boiling point of 84° C. at 22 mm Hg and having the confirmed structure $Pe_cOSi(OMe)_3$.

That which is claimed is:

1. A cycloalkoxysilane having the structure $$(R'O)_x(R')_y Si(OR)_{4-x-y}$$

wherein R is independently selected from the group consisting of alkyl radicals having 1 to 5 carbon atoms and acyl radicals having 2 to 5 carbon atoms. R' is independently selected from the group consisting of a cyclopentyl radical, a cyclohexyl radical a cycloheptyl radical, and substituted radicals thereof, x is 1, 2, 3 or 4 and y is 0, 1 or 2.

2. The cycloalkoxysilane of claim 1, wherein R is selected from the group consisting of methyl, ethyl and propyl radicals.

3. The cycloalkoxysilane of claim 2, wherein y=0.

4. The cycloalkoxysilane of claim 3, wherein R' is selected from the group consisting of a cyclopentyl radical, a cyclohexyl radical and a cycloheptyl radical.

5. The cycloalkoxysilane of claim 4, wherein R' is a cyclopentyl radical and x is 1 or 2.

6. The cycloalkoxysilane of claim 5, wherein R is a methyl radical.

7. The cycloalkoxysilane of claim 2, wherein y=1.

8. The cycloalkoxysilane of claim 7, wherein R' is selected from the group consisting of a cyclopentyl radical, a cyclohexyl radical and a cycloheptyl radical.

9. The cycloalkoxysilane of claim 8, wherein R' is a cyclopentyl radical and x is 1 or 2.

10. The cycloalkoxysilane of claim 9, wherein R is a methyl radical.

* * * * *